United States Patent [19]

Zennaro et al.

[11] Patent Number: 6,121,190

[45] Date of Patent: Sep. 19, 2000

[54] CATALYTIC COMPOSITION USEFUL IN THE FISCHER-TROPSCH REACTION

[75] Inventors: Roberto Zennaro; Andrea Gusso, both of Venice, Italy

[73] Assignees: Agip Petroli S.p.A.; ENI S.p.A., both of Rome, Italy; Institut Francais du Petrole, Rueil Malmaison, France

[21] Appl. No.: 09/015,271

[22] Filed: Jan. 29, 1998

[30] Foreign Application Priority Data

Jan. 30, 1997 [IT] Italy .................................. MI97A0170

[51] Int. Cl.⁷ .............................. B01J 23/46; C07C 27/00
[52] U.S. Cl. .......................... 502/326; 502/325; 502/327; 502/328; 502/329; 502/332; 502/340; 502/349; 502/352; 502/353; 502/354; 518/700; 518/715
[58] Field of Search .................... 502/325, 326, 502/327, 328, 329, 332, 340, 349, 352, 353, 354; 518/700, 715

[56] References Cited

U.S. PATENT DOCUMENTS 4,199,438  4/1980  Antos .
4,284,531  8/1981  Simpson et al. ........................ 502/126
4,381,257  4/1983  Antos ...................................... 502/126
4,609,679  9/1986  Wood et al. .
5,482,910  1/1996  Bricker et al. .......................... 502/300

FOREIGN PATENT DOCUMENTS 0 581 619  2/1994  European Pat. Off. .
2 524 339  7/1983  France .

OTHER PUBLICATIONS

Database WPI, Derwent Publications, AN 87–174456, JP 62–106030, May 16, 1987.

*Primary Examiner*—Elizabeth D. Wood
*Attorney, Agent, or Firm*—Oblon, Spivak, McClelland, Maier & Neustadt, P.C.

[57] ABSTRACT

Catalytic composition comprising a larger quantity of Cobalt, in metal form or in the form of a derivative, and smaller quantities of Ruthenium and Tantalum, in metal form or in the form of a derivative, the above elements being dispersed on a carrier selected from the oxides of at least one of the elements selected from Si, Ti, Al, Zn, Sn, Mg.

14 Claims, No Drawings

CATALYTIC COMPOSITION USEFUL IN THE FISCHER-TROPSCH REACTION

BACKGROUND OF THE INVENION

The present invention relates to a catalytic composition which can be used in effecting the preparation reaction of hydrocarbons by means of the Fischer-Tropsch synthesis; it also relates to the catalytic process for the preparation of hydrocarbons which comprises its use.

FIELD OF THE INVENTION

In particular, the present invention relates to a new catalytic composition containing cobalt, promoted by ruthenium and tantalum, obtained by reacting derivatives of the above elements in the presence of a suitable carrier consisting of an oxidic material as illustrated hereunder. This composition is effective in the conversion of the synthesis gas to hydrocarbon products, with a high selectivity to liquid and waxy, essentially linear paraffinic products.

The selection of cobalt as main constituent of the active phase is due to the fact that this favours the formation of saturated linear hydrocarbons with a high molecular weight, with respect for example to more economical systems based on iron. The use of higher temperatures on the one hand favours the conversion of the synthesis gas but on the other hand hinders the formation of higher hydrocarbons to the advantage of lighter fractions.

DESCRIPTION OF THE RELATED ART

The known art mentions numerous examples of catalysts based on cobalt used for the synthesis of paraffinic products with different distributions.

From the first works of Fischer in 1932 (H.H. Storch, N. Golumbic, R.B. Anderson, "The Fischer Tropsch and Related Synthesis", John Wiley & Son, Inc., New York, 1951), which describe the development of a $Co/ThO_2/MgO$ system supported on kieselguhr, up to the present day, patented systems based on cobalt are essentially: $Co/Mg/ThO_2$ supported on kieselguhr (1954, Reinpruessen A.G.), Co/MgO supported on bentonite (1958, M.W. Kellog), Co/Th/Mg (1959, Rurchemie), Co/Th supported on Silica-gel (1960, Esso Res. & Eng.), Co/Mg/Zr/Kieselguhr (1968, SU-A-660.324, Zelinskii INST.), Co/Ru/Kieselguhr (1976, U.S. Pat. No. 4.088.671 GULF), $Co/Zr/SiO_2$ (1980, GB-A-2.073.237, Shell), Co/Ru supported on Titania (1988, U.S. Pat. No. 4.738.948 Exxon), Co/Re/REO,K supported on Alumina (1988, EP-A-313.375, Statoil), $Co/Mo,W/K,Na/SiO_2$ (1991, GB-A-2.258.414, IFP), $Co/Ru/Cu/K,Sr/SiO_2$ (1993, EP-A-581.619, IFP).

The effect of the promoters on the system based on cobalt is manifold but can be subdivided however into various groups in relation to the function of the promoter itself (B. Jager, R. Espinoza in Catalysis Today 23, 1995, 21–22).

For example promoters such as K, Na, Mg, Sr, Cu, Mo, W and metals of group VIII basically increase the activity. Ru, Zr, rare earth oxides (REO), Ti increase the selectivity to hydrocarbons with a high molecular weight. Ru, REO, Re, Hf, Ce, U and Th favour the regeneration of the catalyst. Among the various promoters ruthenium is certainly the most widely used.

The most recent evolution in catalytic systems for the synthesis of hydrocarbons has aimed at increasing both their activity, in terms of conversion of the reaction reagents, and the selectivity to linear hydrocarbons with a high molecular weight. This has been made possible by the identification of various promoters to be coupled with cobalt, some of which are mentioned in the brief review above.

This evolution has been developed mainly in the last twenty years. In fact, the increase in the price of crude oil in the 1970s' motivated the exploration of other ways of producing liquid fuels and chemicals, one possibility being the transformation of hydrocarbon products with a high molecular weight (waxes) obtained by the Fischer-Tropsch synthesis.

As far as the Fischer-Tropsch synthesis is concerned, this can refer to the hydrogenation process of carbon monoxide to produce higher hydrocarbons and oxygenated molecules with a prevalently linear chain.

The wide range of catalysts and modifications of these indicated in the known art and the wide range of operating conditions for the reduction reaction of the carbon monoxide with hydrogen allows considerable flexibility in the selectivity of the products, products ranging from methane to heavy waxes with oxygenated products as by-products. The distribution of the products can be described by the known growth mechanism deduced from a polymerization kinetics determined by Anderson Shultz and Flory (P. Biloen, W.M.H. Sachtler, Advance in Catalysis, Vol. 30, pages 169–171, Academic Press, New York, 1981; R.B. Anderson, Catalysis, Vol. IV, P.H. Emmett ed., Reinhold, New York, 1956). In accordance with this mechanism, with the assumption of restricting the range of products to maximize for example the $C_5-C_{11}$ fraction (gasoline-range, about 56%) selectivities of methane and the gaseous fraction ($c_2-C_4$) of more than 42% would be obtained. In addition the range of products obtained would be essentially paraffinic-linear and olefinic with a low octane number. The only possibility therefore of deviating from the nature imposed by the Fischer-Tropsch polymerization kinetics is to identify catalytic systems which do not obey said kinetics. An example are systems which basically combine the properties of Fischer-Tropsch catalysts with the shape selectivity of zeolites (U.S. Pat. No. 4.157.338).

The possibility of maximizing the selectivity to heavy liquids and waxes (essentially paraffinic and without sulfur) offers on the other hand many advantages. More specifically, by maximizing the paraffinic liquid-solid fraction it is possible to minimize the selectivity to methane and gas fraction, one of the greatest problems in the case of direct synthesis to gasolines ($C_5-C_{11}$) and light olefins ($C_2-C_4$). By subsequent treatment (e.g. hydrocracking) of this liquid-solid fraction, a high quality medium distillate is obtained compared to the middle distillate obtained from petroleum (Ball J., Gas. Matters, Apr. 27, 1989, pages 1–8). Finally catalysts with a reduced water gas shift activity and low reaction temperature, such as catalysts based on cobalt, have low selectivities to $CO_2$, above all if compared to catalysts based on iron.

Among the factors capable of influencing the distribution of the products, apart from the nature of the catalyst, the reaction conditions should also be taken into consideration. In general, an increase in the temperature causes a lowering of the selectivity to higher hydrocarbons ($C_{12+}$, $C_{22+}$) and a higher conversion of the synthesis gas. Viceversa an increase in the hourly volumetric flow-rate of the synthesis gas (GHSV) determines a decrease in both the conversion of the reagent gas and the probability of propagation of the hydrocarbon chain on the surface of the catalyst, in other words a decrease in the selectivity to higher hydrocarbons. There are therefore limits of selectivity and conversion which impose precise ranges of practicability to the reaction conditions to be adopted.

SUMMARY OF THE INVENTION

The present invention therefore relates to an improved catalytic composition based on cobalt with respect to those of the prior art, as it allows conversions of the mixture of Co and $H_2$ to be obtained (using $SiO_2$ as carrier) in the presence of or without $CO_2$, known as synthesis gas, into linear saturated hydrocarbons containing from 75% to 85% by weight of $C_{5+}$, from 38% to 52.0% by weight of $C_{14+}$, together with selectivities to methane of less than 11.5% and with a productivity of $C_{2+}$ of more than 310 $gC_{2+}/Kg_{cat}*h$.

In accordance with this, the present invention relates to a catalytic composition comprising a greater quantity of Cobalt, in metal form or in the form of a derivative, and smaller quantities of Ruthenium and Tantalum, in metal form or in the form of a derivative, preferably in the form of an oxide, the above elements being dispersed on a carrier selected from the oxides of at least one of the elements selected from Si, Ti, Al, Zn, Zr, Sn, Mg.

DETAILED DESCRIPTION OF THE INVENTION

The content of the above elements in the final catalyst, expressed as metal form of these and defined as weight percentage with respect to the weight of the catalyst, varies within the following ranges:

| Element | Range | Preferred range |
|---|---|---|
| COBALT | 1–50 | 5–35 |
| RUTHENIUM | 0.05–5 | 0.1–3 |
| TANTALUM | 0.05–5 | 0.1–3 |

As mentioned above, the inert carrier of the catalytic composition of the present invention is selected from the oxides of at least one of the elements selected from Si, Ti, Al, Zn, Zr, Sn, Mg, and relative mixtures. The inert carrier which can be used is independent of the crystallographic structure of the above oxides. For example, all types of alumina such as γ, η, δ, θ, κ, α, and relative mixtures, can be used.

When the inert carrier essentially consists of $TiO_2$, the latter can either be in the form of rutile and/or anatase.

In the preferred embodiment, the inert carrier essentially consists of silica.

The cobalt, ruthenium and tantalum can be deposited using various methods well-known to experts in the field such as, for example, ion exchange, impregnation, dry impregnation (also called incipient imbibition), precipitation and coprecipitation, gelation and mechanical mixing.

In the preferred embodiment, the cobalt is deposited on the inert carrier using the dry impregnation technique. According to this method the inert carrier is put in contact with a volume of solution, preferably aqueous, of a salt of cobalt practically equal to the pore volume.

With respect to the deposition of ruthenium and tantalum, this is preferably carried out with the impregnation technique. According to this method the inert carrier, onto which the cobalt was previously deposited, is totally covered with a solution, preferably non-aqueous, of salts of ruthenium and/or tantalum.

A further object of the present invention therefore relates to a process for the preparation of the catalytic composition of the present invention which comprises a first deposition on the inert carrier, preferably via dry impregnation, of a Cobalt salt and subsequently a second and third deposition of a Ruthenium salt and Tantalum salt, preferably via impregnation; the second and third impregnation possibly being carried out inversely or contemporaneously; the above inert carrier preferably being silica.

In the preferred embodiment, the process of the present invention comprises the following steps:

a) production of a first catalytic precursor (A) containing Cobalt and at least part of the inert carrier, by dry deposition of Cobalt on the inert carrier; subsequent calcination, reduction and passivation of the inert carrier containing Cobalt;

b) production of a second catalytic carrier (B) containing Cobalt, Ruthenium and at least part of the inert carrier, by deposition of ruthenium on the first catalytic precursor (A) according to the impregnation technique; subsequent calcination, reduction and passivation of the inert carrier containing Cobalt and Ruthenium;

c) production of the final catalytic composition by deposition of Tantalum on the catalytic precursor (B) according to the impregnation technique, subsequent calcination, reduction and passivation of the inert carrier containing Cobalt, Ruthenium and Tantalum; steps (b) and (c) possibly being carried out inversely or contemporaneously.

Some of the operating details will be more evident on reading the experimental examples provided, whose technicality however, should not be considered as limiting the catalytic compositions of the present invention.

As already specified, the present invention also relates to a process for the preparation of hydrocarbons from synthesis gas in the presence of the catalytic system described above.

The conditions for using these catalysts are, in turn, those known in the art for the embodiment of the Fischer-Tropsch synthesis.

The conversion of the synthesis gas into hydrocarbons takes place at a pressure normally of between 1 and 150 bars, preferably from 10 to 100 bars, at a temperature generally within the range of 150 to 350° C., preferably from 170 to 300° C., even more preferably from 200° C. to 240° C. The hourly volumetric rate is generally from 100 to 20,000, preferably from 400 to 5,000, volumes of synthesis gas per volume of catalyst per hour. The ratio $H_2/CO$ in the synthesis gas is generally from 1:1.5 to 5:1, preferably from 1.2:1 to 2.5:1.

The catalyst can be used in the form of fine powder (10–700 μm approximately) or in the form of particles having an equivalent diameter of from 0.7 to 10 mm, respectively in the presence of a liquid phase (under the operating conditions) and a gaseous phase, or a gaseous phase. The liquid phase can consist of at least one hydrocarbon having at least 5, preferably at least 15, carbon atoms per molecule. In the preferred embodiment, the liquid phase essentially consists of the same reaction product.

For purely illustrative purposes, it can be mentioned that the catalysts of the present invention can be used in a fixed bed reactor, fed in continuous with a mixture of CO and $H_2$ and operating under the following conditions:

reaction temperature: 200–240° C.

reaction pressure: 20 bars space velocity (GHSV): 500–1500 $h^{-1}$ mixture $H_2/CO$: 2/1

The reaction temperature is set so as to obtain a conversion at least 45% higher than the volume of the fed carbon monoxide (conv.CO%).

Following these conditions, the catalysts prepared in examples 1 to 4 were evaluated, whose compositions are summarized in table 1.

The results of the reactivity tests are indicated in tables 2 and 3.

EXAMPLE 1 Reference Catalyst A (Co/Ru/SiO$_2$ 15% Co, 0.2% Ru)

A silica carrier (having a surface area of 520 m$^2$/g, specific pore volume of 0.8 m$^3$/g, average particle diameter of 0.5 mm, specific weight of 0.42 g/ml) is dry impregnated with a nitric solution of Co(NO$_3$)$_2$*6H$_2$O in such quantities as to obtain a percentage of Co equal to 15% by weight with respect to the total. The silica thus impregnated is dried at 120° C. for 16 hours, calcined at 400° C. in air for 4 hours, then treated in a stream of H$_2$ at a space velocity (GHSV) of 1000 h$^{-1}$ inside a tubular reactor at 400° C. for 16 hours. The sample thus reduced is passivated in a mixture of (1%)O$_2$/(99%)N$_2$ with GHSV of 1000 h$^{-1}$ for 2 hours at room temperature.

A 7.5 10$^{-3}$ M solution of Ru(NO$_3$)$_3$*xH$_2$O obtained with the following procedure: precipitation in the form of hydroxide at pH=7.2 of RuCl$_3$*xH$_2$O, subsequent elimination of the chlorides, redissolution in conc. HNO$_3$ and dilution in CH$_3$COCH$_3$ in a ratio 1:250 v/v, is added to the monometallic sample Co/SiO$_2$.

The acetone solution of ruthenium is added to the sample in such a quantity as to have 0.2% of Ru by weight with respect to the total. The slurry is left under stirring for 2 hours and then dried under vacuum at 40° C. This is followed by a calcination phase in air at 350° C. for 4 hours and reduction/passivation analogous to that described above.

EXAMPLE 2 Catalyst B (Co/Ru/Ta/SiO$_2$=15% Co, 0.2% Ru, 0.2% Ta).

For the preparation of the catalyst B, a solution of Ta(EtO)$_5$ 0.01 M in ethanol is added to 50 g of catalyst A in such a volume as to obtain a final weight percentage of tantalum equal to 0.2%.

The suspension thus obtained is left under stirring for two hours and then dried under vacuum at 40° C.

The sample is calcined at 350° C. for 4 hours in air, reduced to 400° C. in H$_2$ with GHSV equal to 1000 h$^{-1}$ and passivated in (l%)O$_2$/(99%)N$_2$ with GHSV of 1000 h$^{-1}$ at room temperature.

EXAMPLE 3 Catalyst C (Co/Ru/Ta/SiO$_2$=15% Co, 0.2% Ru, 0.5% Ta).

The preparation of the catalyst C differs from that described in example 2 in the use of a solution of Ta(EtO)$_5$ 0.01 M in ethanol in such a volume as to obtain a final weight percentage of tantalum equal to 0.5%.

EXAMPLE 4 Catalyst D (Co/Ru/Ta/SiO$_2$=15% Co, 0.2% Ru, 0.9% Ta).

The preparation of the catalyst D differs from that described in example 2 in the use of a solution of Ta(EtO)$_5$ 0.01 M in ethanol in such a volume as to obtain a final weight percentage of tantalum equal to 0.9%.

CATALYTIC TESTS

EXAMPLE 5 Evaluation of the Catalytic Activity of Reference Catalyst A.

Catalyst A, reduced and passivated according to what is described in example 1, is formed in particles having a diameter of from 0.35 to 0.85 mm and subsequently diluted with an inert solid, silicon carbide, having the same particle size as the catalyst and in a volumetric ratio equal to 1:2 catalyst/inert solid. The catalyst thus diluted is then charged into a tubular reactor and subjected to an activation process in a stream of hydrogen (2000 Nl/h•l$_{cat}$) and nitrogen (1000 Nl/h•l$_{cat}$), at a temperature of 300° C. and pressure of 1 bar for 16 hours. The temperature is then lowered to 180° C., the volumetric flow-rate of hydrogen and nitrogen is varied (333–1000 Nl/h•l$_{cat}$) and (5000–15000 Nl/h•l$_{cat}$) respectively, the system pressurized to 20 bars and the carbon monoxide (116.5–500 Nl/h•l$_{cat}$) is then introduced to obtain a volumetric ratio H$_2$/CO equal to 2.

The flow-rate of nitrogen in the starting-up phase of the reaction is progressively lowered until complete elimination according to the following sequence (the lower flow-rates refer to the tests with GHSV=500 h$^{-1}$, the higher flow-rates to GHSV=1500 h$^{-1}$):

| time (hours) | H$_2$ flow-rate (Nl/h · 1$_{cat}$) | CO flow-rate (Nl/h · 1$_{cat}$) | N$_2$ flow-rate (Nl/h · 1$_{cat}$) |
|---|---|---|---|
| 0 | 333–1000 | 166.5–500 | 5000–15000 |
| 1 | 333–1000 | 166.5–500 | 3750–11250 |
| 2 | 333–1000 | 166.5–500 | 2500–7500 |
| 3 | 333–1000 | 166.5–500 | 1250–3750 |
| 4 | 333–1000 | 166.5–500 | 0 |

At the end of the starting-up phase, the reaction temperature is regulated so as to obtain a conversion of the carbon monoxide with respect to the volume fed (conv.Co%) of less than 20% for at least 48 hours, then in the following 48 hours the temperature is progressively increased until a minimum CO conversion value of 45% is reached without exceeding however the reaction temperature of 240° C., in order to minimize the production of methane as well as the gaseous fractions (C$_2$–C$_4$).

As indicated in table 2, on increasing the volumetric flow-rates of the mixture H$_2$-CO (GHSV from 500 h$^{-1}$ to 1500 h$^{-1}$) it is necessary to increase the reaction temperature (from 200° C. to 240° C.) to reach CO conversions higher than the limit of 45%. This is to the advantage of the selectivity to methane (from 7.8% to 29.7%), expressed as percentage referring to the total carbon present in the products (C%), and disadvantage of the selectivities to higher hydrocarbons (C$_{14+}$: from 44.6% to 25.3%, C$_{9+}$: from 66.9% to 48.8%), expressed as percentage referring to the total weight of the whole hydrocarbon fraction produced (wt %).

EXAMPLE 6 Evaluation of the Catalytic Activity of Catalysts B, C and D.

The catalysts of the present invention B, C and D, containing tantalum in varying percentages, are subjected to a catalytic activity test. The activation and starting conditions are completely analogous to what is described in example 5.

As shown in table 3, with a total volumetric flow-rate (GHSV) equal to 1500 h$^{-1}$ and reaction temperatures of less than 210° C., CO conversions of more than 67% are obtained together with hourly weight productivities of hydrocarbons with more than two carbon atoms (C$_{2+}$) of more than 311 gC$_{2+}$/Kg$_{cat}$•h, selectitivies to methane of less than 11.2%, selectivities to C$_{14+}$hydrocarbons of from 40.4% to 48.7%, C$_{9+}$hydrocarbons of from 70.5% to 76.7% and finally selectivities to C$_{5+}$of between 79.7% and 81.7%.

The above results clearly show the advantages of the catalysts of the present invention with respect to those of the prior art.

EXAMPLE 7 Catalysts supported on TiO$_2$

Following the procedures described above a reference catalyst E is prepared completely similar to catalyst A, but having TiO$_2$ as a carrier instead of SiO$_2$. In this case the TiO$_2$ had a surface area of 25 m$^2$/g, a specific pore volume of 0.31 cm$^3$/g and a content of rutile equal to 81%.

The catalyst E has the composition, in weight percentage, Co/Ru/TiO$_2$: Co=12%, Ru=0.2%.

The catalyst F is prepared in the same way as described for the preparation of catalyst B, having, again in weight percentage, the composition Co/Ru/Ta/TiO$_2$: Co=12%, Ru=0.2%, Ta=0.2%.

The results of the experiments carried out in the presence of these catalysts are indicated in table 4.

Also in this case there is an improvement in the selectivity to heavier hydrocarbons and a lower selectivity to methane in the case of the catalyst promoted with tantalum ($C_{22+}$=26.2%, $C_{9-}$=85.4%, $C_{5+}$=89.5%, $CH_4$=6.7%) with respect to the catalyst without tantalum ($C_{22+}$=18.1%, $C_{9+}$=74.3%, $C_{5+}$=85.7%, $CH_4$ =8.7%)

The improvement however is lower than that of the catalysts supported on silica.

TABLE 1

| Example | Cat. | % Co | % Ru | % Ta | Carrier |
|---|---|---|---|---|---|
| 1 | A | 15 | 0.2 | — | SiO$_2$ |
| 2 | B | 15 | 0.2 | 0.2 | SiO$_2$ |
| 3 | C | 15 | 0.2 | 0.5 | SiO$_2$ |
| 4 | D | 15 | 0.2 | 0.9 | SiO$_2$ |

TABLE 2

Comparative Example 5
Catalyst A:

| | Reaction Temperature | | |
|---|---|---|---|
| | 200 | 220 | 240 |
| GHSV h$^{-1}$ | 500 | 1000.0 | 1500 |
| Conv. CO (%) | 48.5 | 51.3 | 47.1 |
| Prod. C$_{2+}$ (g/Kg h) | 81.4 | 149.0 | 183.5 |
| CH$_4$ (C %) | 7.8 | 18.8 | 29.7 |
| CO$_2$ (C %) | 0.3 | 1.8 | 2.2 |
| C$_1$–C$_4$ (wt %) | 13.5 | 32.7 | 49.0 |
| C$_{22+}$ (wt %) | 14.1 | 15.4 | 3.2 |
| C$_{14+}$ (wt %) | 44.6 | 40.0 | 25.3 |
| C$_{9+}$ (wt %) | 66.9 | 64.1 | 48.8 |
| C$_{5+}$ (wt %) | 86.5 | 67.3 | 51.0 |

TABLE 3

| | Example 6 | | |
|---|---|---|---|
| | Cat. B | Cat. C | Cat. D |
| % Tantalum | 0.2 | 0.5 | 0.9 |
| Reaction Temp. | 206 | 209 | 206 |
| GHSV h$^{-1}$ | 1500 | 1500 | 1500 |
| Conv. CO (%) | 69.1 | 67.4 | 68.2 |
| Prod. C$_{2+}$ (g/Kg h) | 326.2 | 311.5 | 311.8 |
| CH$_4$ (C %) | 11.2 | 10.5 | 10.0 |
| CO$_2$ (C%) | 0.1 | 0.9 | 0.1 |
| C$_1$–C$_4$ (wt %) | 19.0 | 20.3 | 18.3 |
| C$_{22+}$ (wt %) | 11.3 | 15.1 | 13.9 |
| C$_{14+}$ (wt %) | 40.4 | 48.5 | 48.7 |
| C$_{9+}$ (wt %) | 70.5 | 73.1 | 76.7 |
| C$_{5+}$ (wt %) | 81.0 | 79.7 | 81.7 |

TABLE 4

| | Example 7 | |
|---|---|---|
| | Catalyst | |
| | E | F |
| Composition | Co/Ru/TiO$_2$ | Co/Ru/Ta/TiO$_2$ |
| Reaction Temp. | 224 | 217 |
| GHSV h$^{-1}$ | 1500 | 1500 |
| Conv. CO (%) | 59.9 | 60.2 |
| Prod. C$_{2+}$ (g/Kg h) | 157.5 | 157.5 |
| CH$_4$ (C %) | 8.7 | 6.7 |
| CO$_2$ (C%) | 0.2 | 0.1 |
| C$_1$–C$_4$ (wt %) | 14.3 | 10.5 |
| C$_{22+}$ (wt %) | 18.1 | 26.2 |
| C$_{14+}$ (wt %) | 49.8 | 70.4 |
| C$_{9+}$ (wt %) | 74.3 | 85.4 |
| C$_{5+}$ (wt %) | 85.7 | 89.5 |

The Italian priority application No. MI97 A 000170 is herein incorporated by reference.

What is claimed is:

1. A catalytic composition comprising from about 12 to 50% of Cobalt, in metal form or in the form of a derivative, from 0.05–5% of Ruthenium and from 0.05–5% Tantalum, each in metal form or in the form of a derivative, the above elements being dispersed on an inert carrier selected from the oxides of at least one of the elements selected from Si, Ti, Al, Zn, Sn, or Mg, the percentages being based on the weight of said composition.

2. The catalytic composition according to claim 1, wherein the Ruthenium and Tantalum are in the form of oxides.

3. The catalytic composition according to claim 1, wherein the cobalt is present in a quantity of up to 35% by weight.

4. The catalytic composition according to claim 1, wherein the ruthenium and tantalum are each present in a quantity of from 0.1 to 3% by weight.

5. The catalytic composition according to claim 1, characterized in that the carrier essentially consists of SiO$_2$.

6. A process for the preparation of the catalytic composition according to claim 1, which comprises initially depositing on the inert carrier a Cobalt salt and subsequently depositing on the carrier a Ruthenium salt and a Tantalum salt; the subsequent deposition being carried out sequentially or simultaneously.

7. The process according to claim 6, wherein the Cobalt salt is deposited on the inert carrier by dry impregnation.

8. The process according to claim 6, wherein the Ruthenium and Tantalum salts are deposited by impregnation.

9. The process according to claim 6, characterized in that it comprises the following steps:

a) dry deposition of cobalt on at least part of the inert carrier followed by subsequent calcination, reduction and passivation to provide an inert carrier (A) containing cobalt;

b) deposition of Tantalum or Ruthenium on at least part of the inert carrier (A) followed by subsequent calcination, reduction and passivation to provide inert carrier (B) containing Cobalt and Tantalum or Ruthenium;

c) deposition of Tantalum or Ruthenium on the inert carrier (B) followed by subsequent calcination, reduction and passivation to provide an inert carrier containing cobalt, ruthenium and tantalum.

10. The process according to claim 9, wherein in step (a) the whole of the inert carrier is used.

11. A process for the synthesis of hydrocarbons starting from a mixture essentially consisting of CO and $H_2$, optionally in the presence of $CO_2$, comprising reacting said mixture in the presence of a catalyst according to claim 1.

12. The process for the synthesis of hydrocarbons according to claim 1, wherein the reaction is carried out at a pressure of from 1 to 150 bars and at a temperature of from 150 to 350° C., the ratio $H_2/CO$ being from 1:1.5 to 5:1.

13. The process according to claim 12, characterized in that the reaction is carried out at a pressure of from 10 to 100 bars and at a temperature of from 170° C. to 300° C., the ratio $H_2/CO$ being from 1.2:1 to 2.5:1.

14. The process according to claim 12, characterized in that the reaction is carried out at a temperature of from 200° C. to 240° C.

* * * * *